United States Patent [19]

Nestler

[11] Patent Number: 5,998,645
[45] Date of Patent: Dec. 7, 1999

[54] BLEACHING-ACTIVE METAL COMPLEXES

[75] Inventor: Bernd Nestler, Frankfurt, Germany

[73] Assignee: Clariant GmbH, Frankfurt, Germany

[21] Appl. No.: 09/071,551

[22] Filed: May 1, 1998

[30] Foreign Application Priority Data

May 7, 1997 [DE] Germany ............................ 197 19 397

[51] Int. Cl.$^6$ .............................. C07F 13/00; C07F 15/06
[52] U.S. Cl. ............................ 556/45; 556/150; 502/155; 510/311; 252/186.33; 252/186.38
[58] Field of Search ..................... 556/45, 150; 502/155; 510/311; 252/186.33, 186.38

[56] References Cited

U.S. PATENT DOCUMENTS

| | | | |
|---|---|---|---|
| 2,864,776 | 12/1958 | McCune et al. | 252/138 |
| 2,940,938 | 6/1960 | Blinka | 252/309 |
| 3,368,977 | 2/1968 | Tuvell | 252/137 |
| 3,850,831 | 11/1974 | Edvin et al. | 252/99 |
| 4,087,369 | 5/1978 | Wevers | 252/102 |
| 4,144,226 | 3/1979 | Crutchfield et al. | 528/231 |
| 4,146,495 | 3/1979 | Crutchfield et al. | 252/89 R |
| 4,583,217 | 4/1986 | Kittel | 370/29 |
| 4,728,455 | 3/1988 | Rerek | 252/99 |
| 4,772,412 | 9/1988 | Green et al. | 252/96 |
| 5,114,606 | 5/1992 | Van Vliet et al. | 252/103 |
| 5,114,611 | 5/1992 | Van Kralingen et al. | 252/186.33 |
| 5,244,594 | 9/1993 | Favre et al. | 252/186.33 |
| 5,314,635 | 5/1994 | Hage et al. | 252/102 |

FOREIGN PATENT DOCUMENTS

| | | |
|---|---|---|
| 1102966 | 6/1981 | Canada . |
| 028849 | 5/1981 | European Pat. Off. . |
| 062523 | 10/1982 | European Pat. Off. . |
| 101634 | 2/1984 | European Pat. Off. . |
| 240057 | 10/1987 | European Pat. Off. . |
| 241962 | 10/1987 | European Pat. Off. . |
| 408131 | 1/1991 | European Pat. Off. . |
| 458398 | 11/1991 | European Pat. Off. . |
| 509787 | 10/1992 | European Pat. Off. . |
| 544440 | 6/1993 | European Pat. Off. . |
| 544490 | 6/1993 | European Pat. Off. . |
| 544519 | 6/1993 | European Pat. Off. . |
| 549272 | 6/1993 | European Pat. Off. . |
| 630964 | 12/1994 | European Pat. Off. . |
| 717103 | 6/1996 | European Pat. Off. . |
| 2233771 | 2/1973 | Germany . |
| 19529905 | 2/1997 | Germany . |
| 1205711 | 9/1970 | United Kingdom . |
| 1270040 | 4/1972 | United Kingdom . |
| 1292352 | 10/1972 | United Kingdom . |
| 1370377 | 10/1974 | United Kingdom . |
| 1561333 | 2/1980 | United Kingdom . |
| 2194536 | 3/1988 | United Kingdom . |
| WO 91/14694 | 10/1991 | WIPO . |
| WO 95/30681 | 11/1995 | WIPO . |
| WO 96/15136 | 5/1996 | WIPO . |

OTHER PUBLICATIONS

J. Inorg. Nucl. Chem. 1975, vol. 37, pp. 2005–2006.
A. Bottcher et al., Z. Naturforsch. 49b, 1089–1100 (1994).
Derwent Abstract–WO 95/30681.

European Search Report (1999).
Derwent Patent Family Report and/or Abstract (1999).
XP–000508269 A Practical Method for the Large–Scale Preparation of [N,N'–Bis (3,5–di–tert–butylsalicylidene)–1,2–cyclohexanediaminato(2–)]manganese(III)Chloride, a Highly Enantioselective Epoxidation Catalyst, J.F. Larrow et al., Journal of Organic Chemistry, Bd. 59, Nr.7, Apr. 8, 1994, pp. 1939–1942.

XP–002087896 "A Novel Synthetic Approach to Asymmetric Salen, Dihydrosalen,and Tetrahydrosalen Ligands: Structures and $O_2$–Activating Properties of their Nickel (II) and Cobalt (II) Complexes," Böttcher et al., Z. Naturforschung, Nr. 49b, 1994, pp. 1089–1100.

Mikuriya et al., Chemistry Letters, pp. 1571–1574, 1992.

Chemical Abstracts, abstract No. 32379, vol. 101, 1984.

Li et al., Inorg. Chem., vol. 18, No. 18, pp. 3401–3410, 1989.

*Primary Examiner*—Porfirio Nazario-Gonzalez
*Attorney, Agent, or Firm*—Miles B. Dearth

[57] ABSTRACT

Compounds of the following formula are suitable as activators for peroxy compounds in laundry detergents and cleaning products:

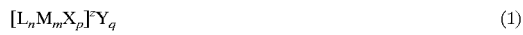

in which

M is manganese in oxidation stage II, III, IV, V and/or VI or cobalt in oxidation stage II and/or III, and iron in oxidation stage II and/or III, X is a coordination group or bridging group, Y is a counterion in the corresponding stoichiometric amount to balance a charge z present, where z as the metal complex charge can be positive, zero or negative, n and m, independently of one another, are integers from 1 to 4, p is an integer from 0 to 15, q is z/charge of Y and L is a ligand of the formula (2)

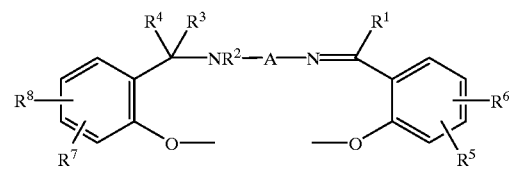

in which substituents $R^1$ to $R^8$ are as defined in the description, and A is a $C_2$–$C_4$-alkylene, $C_5$–$C_{10}$-cycloalkylene or amino group.

16 Claims, No Drawings

BLEACHING-ACTIVE METAL COMPLEXES

It is known that the bleaching power of peroxidic bleaches in laundry detergents and cleaning products, such as hydrogen peroxide, perborates, percarbonates, persilicates and perphosphates, and thus the full efficiency of these bleaches for removing tea, coffee, fruit or red wine stains is only attained at relatively high temperatures of significantly above 60° C. To improve the severely reduced bleaching effect at lower temperatures, especially below 60° C., it is possible to use compounds to activate the peroxide bleaches. A number of transition metal salts and corresponding complexes with mostly chelating compounds have been proposed for this purpose, although the effectiveness of a metal or a specific combination of transition metal and complex ligand is not predictable.

Such metal complexes for activating peroxy compounds are described in U.S. Pat. Nos. 4,728,455, 5,314,635, 5,244,594, 5,114,611, 5,114,606, EP 549272, EP 544519, EP 544490, EP 544440, EP 509787, EP 458398, WO 9615136, EP 717 103, EP 630 964, EP 408 131 and WO 95/30681.

Neutral metal complexes containing bis(2-hydroxybenzylidene)-2,6-pyridinediamine as ligand are also known, from J. Inorg. Nucl. Chem. 1975, Vol. 37, pp. 2005–2006.

The present invention relates to previously unknown compounds of the formula 1

$$[L_n M_m X_p]Y_q \qquad (1)$$

in which
- M is manganese in oxidation stage II, III, IV, V and/or VI or cobalt in oxidation stage II and/or III, or iron in oxidation stage II and/or III,
- X is a coordination group or bridging group,
- Y is a counterion in the corresponding stoichiometric amount to balance a charge z present, where
- z as the metal complex charge can be positive, zero or negative,
- n and m, independently of one another, are integers from 1 to 4,
- p is an integer from 0 to 15,
- q is z/charge of Y
- L is a ligand of the formula (2)

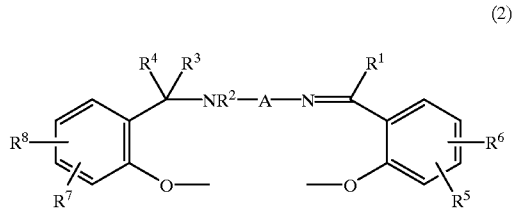

in which
- $R^1$, $R^2$, $R^3$ and $R^4$ independently of one another are hydrogen, $C_1$- to $C_{10}$-alkyl, cycloalkyl or aryl radicals,
- $R^5$, $R^6$, $R^7$, $R^8$ independently of one another are hydrogen, $C_1$- to $C_{30}$-alkyl, cycloalkyl or aryl radicals, $C_1$- to $C_4$-alkoxy groups, substituted or unsubstituted amino or ammonium groups, halogen atoms, sulfo groups, carboxyl groups, or groups of the formula —$(CH_2)_r$—COOH,—$(CH_2)_r$—$SO_3H$,—$(CH_2)_r$—$PO_3H_2$,—$(CH_2)_r$—OH, in which r and I are integers from 0 to 4, and the specified acid groups may also be in salt form,
and
- A is a $C_2$–$C_4$-alkylene, $C_5$–$C_{10}$-cycloalkylene or arylene group.

x is preferably one of the following groups:
  $F^-$, $Cl^-$, $Br^-$, $SCN^-$, $OH^-$, $O_2^{2-}$, $O^{2-}$, $O_2^-$, $HOO^-$, $R^9OO^-$, $H_2O$, $SH^-$, $CN^-$, $OCN^-$, $S^{2-}$, $N_3^-$, $NH_3$, $NR^9_3$, $NR^9_2{}^-$, $R^9O^-$, $R^9COO^-$, $R^9SO_3^-$ and $R^9SO_4^-$, in which $R^9$ is in each case hydrogen, $C_1$- to $C_8$-alkyl, cycloalkyl or $C_6$- to $C_{18}$-aryl. The counterion Y is preferably an ion of the following formulae:
  when z is positive: $F^-$, $Cl^-$, $Br^-$, $NO_3^-$, $ClO_4^-$, $SCN^-$, $PF_6^-$, $R^9SO_4^-$, $R^9COO^-$, $R^9SO_3^-$, $BF_4^-$, $BPh_4^-$, $SO_4^{2-}$ and $SO_4^{2-}$;
  when z is negative: $Li^+$, $Na^+$, $K^+$, $Mg^{2+}$, $Ca^{2+}$, $Al^{3+}$, $NH_4^+$, $R^9NH_3^+$, $R^9_2NH_2^+$, $R^9_3NH^+$ and $R^9_4N^+$,
in which $R^9$ is as defined above.

M is preferably manganese,
$R^1$, $R^2$, $R^4$, $R^7$ and $R^8$ are preferably hydrogen,
$R^3$ is preferably hydrogen or methyl,
$R^5$ is preferably $C_1$–$C_4$-alkyl, $C_1$–$C_4$-alkoxy or a substituted or unsubstituted amino or ammonium group, in particular di-$C_1$–$C_4$-alkylamino groups,
$R^6$ is preferably hydrogen or methyl and
A is preferably ethylene and cyclohexylene.

The ligands of the formula 2 are prepared by reacting N-(2-hydroxybenzyl)diamino compounds with correspondingly substituted salicylaldehydes according to the details in A. Böttcher et al., Z. Naturforsch. 49b, 1089–1100 (1994). The metal complexes according to the invention are prepared by reacting Mn salts, Co salts or Fe salts with these ligands again according to the details at this literature reference.

The novel mono- or polycyclic complexes of the formula 1 are highly suitable as bleach and oxidation catalysts, in particular in laundry detergents and cleaning products and in textile and paper bleaching. Particular emphasis is to be placed here on textile detergents in the form of pulverulent detergents or as liquid formulations and dishwashing detergents. One advantage of the novel bleach catalysts is their stability to hydrolysis and oxidation and their catalytic effect even at low temperatures. They improve not only the bleaching effect of hydrogen peroxide in such formulations, but also that of organic and inorganic peroxy compounds.

Accordingly, the present invention also provides a process for bleaching soiled substrates, which comprises bringing the soiled substrate in an aqueous bleach liquor into contact with peroxy compounds and an effective amount of one or more of the novel metal complexes as bleach catalysts.

The aqueous bleach liquor preferably comprises these metal complexes, based on the weight of the bleach liquor, in an amount of from 0.001 to 100 ppm of metal, in particular from 0.01 to 50 ppm of metal, especially from 0.03 to 20 ppm of metal (ppm means parts per million, based on the weight). Higher contents of metal complexes, for example up to 500 ppm, can be advantageous in industrial bleaching processes, for example in the textile or paper sector. The low metal contents specified at the beginning refer principally to household textile detergents.

The invention also provides for the use of these bleach catalysts in bleaching laundry detergents and cleaning compositions. In addition to a peroxide compound or a peroxide-releasing compound and the bleach catalyst, these laundry detergents and cleaning compositions also customarily comprise surface-active compounds and other known ingredients.

Suitable peroxides and peroxide-releasing compounds are alkali metal peroxides, organic peroxides, such as urea-hydrogen peroxide adducts, and inorganic per salts, such as alkali metal perborates, percarbonates, perphosphates, persilicates and persulfates. Particular preference is given to sodium perborate tetrahydrate and, in particular, sodium perborate monohydrate. Sodium perborate monohydrate is preferred because of its good shelf life and its good solubility in water. Sodium percarbonate may be preferred for environmental protection reasons. Alkyl hydroperoxides are another suitable group of peroxide compounds. Examples of these substances are cumene hydroperoxide and t-butyl hydroperoxide. Aliphatic or aromatic mono- or dipercarboxylic acids and the corresponding salts are also suitable as peroxy compounds. Examples thereof are peroxy-a-naphthoic acid, peroxylauric acid, peroxystearic acid, N,N-phthaloylaminoperoxycaproic acid, 1,12-diperoxydodecanedioic acid, 1,9-diperoxyazelaic acid, diperoxysebacic acid, diperoxyisophthalic acid, 2-decyidiperoxybutane-1,4-dioic acid and 4,4'-sulfonylbisperoxybenzoic acid. Other suitable peroxy compounds are inorganic peroxy acid salts, e.g. potassium monopersulfate. Mixtures of two or more of these compounds are also suitable.

The novel laundry detergent and cleaning composition formulations usually comprise from 1 to 30% by weight, in particular from 2 to 25% by weight, of peroxy compounds.

In addition to the peroxy compounds, the laundry detergents and cleaning compositions may additionally comprise bleach activators in customary amounts (from about 1 to 10% by weight).

Examples of such bleach activators are compounds having quaternary ammonium structures, such as, for example, 2-(N,N,N-triethylammonio)ethyl 4-sulfophenyl carbonate, N-octyl-N,N-dimethyl-N-10-carbophenoxydecylammonium chloride, sodium 3-(N,N,N-trimethylammonio)-propyl 4-sulfophenylcarboxylate and N,N,N-trimethylammonium tolyl-oxybenzenesulfonate.

In addition to the aforementioned quaternary ammonium salts, esters such as, for example, acylphenolsulfonates and acylalkylphenolsulfonates and acylamides are preferred bleach activators. Of particular interest here are the compounds sodium 4-benzoyloxybenzenesulfonate, N,N,N',N'-tetraacetylethylenediamine (TAED), sodium 1-methyl-2-benzoyloxybenzene-4-sulfonate, sodium 4-methyl-3-benzoyloxybenzoate, sodium nonanoyloxybenzenesulfonate, sodium 3,5,5-trimethylhexanoyloxybenzenesulfonate, benzoylcaprolactam, 2-phenyl-4H-3,1-benzoxazin-4-one, glucose pentaacetate and tetraacetylxylose and also ketones and nitrilic activators, all of which are preferentially used in practice.

Effective amounts of the metal complexes of the formula 1 present in these laundry detergent and cleaning composition formulations are usually amounts of from 0.0001 to 0.5% by weight of metal, in particular from 0.00025 to 0.25% by weight of metal, especially from 0.0005 to 0.1% by weight of metal, based on the weight of the formulations. These amounts can vary slightly depending on customary practices.

The surface-active substance in the laundry detergents and cleaning compositions can be derived from natural products, such as, for example, soap, or is a synthetic compound selected from the group consisting of anionic, nonionic, amphoteric, (zwitterionic) or cationic surface-active substances, or mixtures thereof. Many suitable substances are available commercially and are described in the literature, for example in "Surface active agents and detergents", Vol. 1 and 2, from Schwartz, Perry and Berch. The total amount of surface-active compounds can be up to 50% by weight, and is preferably from 1% by weight to 40% by weight, in particular from 4% by weight to 25% by weight, of the total laundry detergent or cleaning composition.

Synthetic anionic surface-active substances are usually water-soluble organic alkali metal sulfates and sulfonates having alkyl radicals of from about 8 to 22 carbon atoms, the term "alkyl" including the alkyl substituents of higher aryl radicals.

Examples of suitable anionic detergents are sodium alkylsulfonates and ammonium alkylsulfonates, especially the sulfates obtained by sulfation of higher ($C_8$ to $C_{18}$) alcohols; sodium alkylbenzenesulfonates and ammonium alkylbenzenesulfonates containing a $C_9$- to $C_{20}$-alkyl radical, in particular linear secondary sodium alkylbenzenesulfonates containing a $C_{10}$- to $C_{15}$-alkyl radical; sodium alkyl glycerol ether sulfates, particularly the esters of the higher alcohols derived from tallow oil and coconut oil; the sodium sulfates and sodium sulfonates of the coconut fatty acid monoglycerides; sodium salts and ammonium salts of sulfuric acid esters of higher ($C_9$ to $C_{18}$) oxalkylated fatty alcohols, particularly those oxalkylated using ethylene oxide; the reaction products of the esterification of fatty acids with isethionic acid and subsequent neutralization with sodium hydroxide; sodium salts and ammonium salts of the fatty acid amides of methyltaurine; alkanemonosulfonates such as those from the reaction of α-olefins ($C_8$–$C_{20}$) with sodium bisulfite and those from the reaction of paraffins with $SO_2$ and $Cl_2$ with subsequent basic hydrolysis, in which a mixture of different sulfonates is produced; sodium dialkylsulfosuccinates and ammonium dialkylsulfosuccinates containing $C_7$- to $C_{12}$-alkyl radicals; and olefinsulfonates which are produced in the reaction of olefins, in particular $C_{10}$- to $C_{20}$-α-olefins, with $SO_3$ and subsequent hydrolysis of the reaction products. The preferred anionic detergents are sodium alkylbenzenesulfonates containing $C_{15}$- to $C_{18}$-alkyl radicals, and sodium alkyl ether sulfates containing $C_8$- to $C_{18}$-alkyl radicals.

Examples of suitable nonionic surface-active compounds, which are preferably used together with anionic surface-active compounds, are, in particular, the products of the reaction of alkylene oxides (usually ethylene oxide) with alkylphenols ($C_5$- to $C_{22}$-alkyl radicals), the reaction products generally containing from 5 to 25 ethylene oxide (EO) units in the molecule; the products of the reaction of aliphatic ($C_8$ to $C_{18}$) primary or secondary, linear or branched alcohols with ethylene oxide containing in general from 6 to 30 EO, and the products of the addition of ethylene oxide to reaction products of propylene oxide and ethylenediamine. Other nonionic surface-active compounds are alkylpolyglycosides, long-chain tertiary amine oxides, long-chain tertiary phosphine oxides and dialkyl sulfoxides.

Amphoteric or zwitterionic surface-active compounds can also be used in the compositions according to the invention, although in most cases this is not desired in view of their high cost. If amphoteric or zwitterionic compounds are used, it is usually in small amounts in compositions which primarily comprise anionic and nonionic surfactants.

It is also possible to use soaps in the compositions according to the invention, preferably in an amount of less than 25% by weight. They are particularly suitable in small amounts in binary (soap/nonionic surfactant) or in ternary mixtures together with nonionic or mixed synthetic anionic and nonionic surfactants. The soaps used are preferably the sodium salts, and less preferably the potassium salts, of saturated and unsaturated $C_{10}$- to $C_{24}$-fatty acids or mixtures thereof. The amounts of such soaps can be from 0.5% by weight to 25% by weight, lower amounts of from 0.5% by weight to 5% by weight generally sufficing for foam control. Soap proportions between about 2% and about 20%, particularly between about 5% and about 10%, have a positive effect. This is particularly the case in hard water, where the soap serves as an additional builder substance.

The laundry detergents and cleaning compositions generally also comprise a builder. Suitable builders include: calcium-binding substances, precipitants, calcium-specific ion exchangers and mixtures thereof. Examples of calcium-binding substances include alkali metal polyphosphates, such as sodium tripolyphosphate; nitrilotriacetic acid and water-soluble salts thereof; the alkali metal salts of carboxymethyloxysuccinic acid, ethylenediaminetetraacetic acid, oxydisuccinic acid, mellitic acid, benzopolycarboxylic acids, citric acid; and polyacetal carboxylates, as disclosed in U.S. Pat. Nos. 4,144,226 and 4,146,495. Examples of precipitants are sodium orthophosphate, sodium carbonate and soaps from long-chain fatty acids.

Examples of calcium-specific ion exchangers are the various types of water-insoluble, crystalline or amorphous aluminum silicates, of which zeolites are the most well known examples.

The builder substances can be present in amounts of from 5% by weight to 80% by weight, an amount of from 10% by weight to 60% by weight being preferred.

In addition to the ingredients already mentioned, the laundry detergents and cleaning compositions can comprise conventional additives in amounts usually present in such products. Examples thereof are foam formers, such as, for example, alkanolamides, particularly monoethanolamides from palm kernel oil fatty acids and coconut fatty acids; antifoams, such as, for example, alkyl phosphates and alkyl silicones; antiredeposition agents and similar auxiliaries, such as, for example, sodium carboxymethylcellulose and alkylcellulose ethers or substituted alkylcellulose ethers; stabilizers, such as ethylenediaminetetraacetic acid; fabric softeners for textiles; inorganic salts, such as sodium sulfate; and, in customarily small amounts, fluorescent substances, perfumes, enzymes, such as proteases, cellulases, lipases and amylases, disinfectants and dyes. The bleach catalysts of this invention can be used in a large number of products. These include textile detergents, textile bleaches, surface cleaners, toilet cleaners, automatic dishwashing cleaners and also denture cleaners. The detergents can be in solid form or liquid form.

For reasons of stability and ease of handling, it is advantageous to use the bleach activators in the form of granules which, in addition to the bleach catalyst, comprise a binder. A variety of methods to prepare such granules are described in the patent literature, for example in CA 1,102,966, GB 1,561,333, U.S. Pat. No. 4,087,369, EP 240057, EP 241962, EP 101634 and EP 62523.

The granules comprising the bleach catalysts according to the invention are generally added to the laundry detergent composition together with the other, dry constituents such as, for example, enzymes, and inorganic peroxide bleaches. The laundry detergent composition to which the catalyst granules have been added can be obtained in a variety of ways, such as, for example, by mixing the dry components, extruding or spray drying.

In a further embodiment, the bleach catalysts according to the invention are particularly suitable for non-aqueous liquid laundry detergents, together with a bleaching peroxide compound, for example sodium perborate, in order to give the laundry detergent a substantial cleaning power for fabric and textiles. Such nonaqueous, liquid laundry detergents, which include pasty and gelatinous detergent compositions, are described, for example, in U.S. Pat. Nos. 2,864,770, 2,940,938, 4,772,412, 3,368,977, GB 1,205,711, GB 1,370, 377, GB 1,270,040, GB 30 1,292,352, GB 2,194,536, DE 2233771 and EP 28849. These are compositions in the form of a nonaqueous liquid medium in which a solid phase can be dispersed.

The nonaqueous liquid medium can be a liquid surface-active substance, preferably a nonionic surface-active substance, a nonpolar liquid medium, such as, for example, liquid paraffin, a polar solvent, such as, for example, polyols, for example glycerol, sorbitol, ethylene glycol, possibly in conjunction with low-molecular-weight monohydric alcohols, such as ethanol or isopropanol or mixtures thereof.

The solid phase can comprise builder substances, alkalis, abrasive substances, polymers and solid ionic surface-active compounds, bleaches, fluorescent substances and other customary solid ingredients.

The following examples give an overview of the embodiments of the invention.

EXAMPLE 1

N-(2-Hydroxybenzyl)-N'-(2-hydroxybenzylidene)-1, 2-diaminoethane, manganese complex 28.7 g of salicylicaldehyde were added to a solution of 39.2 g of N-(2-hydroxybenzyl)-1,2-diaminoethane [prepared in accordance with: A. Böttcher et al., Z. Naturforsch. 49b, 1089–1100 (1994)] in 100 ml of isopropanol, and the resulting solution was refluxed for two hours. Cooling the solution produced a solid, and recrystallization from isopropanol gave 49.8 g of N-(2-hydroxybenzyl)-N'-(2-hydroxybenzylidene)-1,2-diaminoethane.

1.35 g of the resulting compound were dissolved in 60 ml of ethanol, and 1.22 g of manganese(II) acetate (tetrahydrate) were added in portions. After stirring for two hours at the boil, the solvent was removed on a rotary evaporator (water-pump vacuum), and the residue was washed with hot isopropanol to give 1.6 g of N-(2-hydroxybenzyl)-N'-(2-hydroxybenzylidene)-1,2-diaminoethane, manganese complex in the form of a dark brown amorphous solid.

EXAMPLE 2

N-(2-Hydroxybenzyl)-N'-(2-hydroxybenzylidene)-1, 2-diaminoethane, manganese complex The N-(2-hydroxybenzyl)-N'-(2-hydroxybenzylidene)-1, 2-diaminoethane, manganese complex was synthesized as described in Example 1; manganese(III) acetate (dihydrate) was used instead of manganese(II) acetate (tetrahydrate) in the reaction.

EXAMPLE 3

N-(2-Hydroxybenzyl)-N'-(2-hydroxybenzylidene)-1 ,2-diamino-cyclohexane, manganese complex The N-(2-hydroxybenzyl)-N'-(2-hydroxybenzylidene)-1, 2-diaminocyclohexane, manganese complex was prepared from N-(2-hydroxybenzyl)-1,2-diaminocyclohexane according to Example 1.

EXAMPLE 4

N-(2-Hydroxybenzyl)-N'-(2-hydroxybenzylidene)-N-methyl-1,2-diaminoethane, manganese complex 8.87 g of dimethyl sulfate were added dropwise over the course of 20 minutes at room temperature to a solution of 16.2 g of N-(2-hydroxybenzyl)-N'-(2-hydroxybenzylidene)-1,2-diaminoethane, 10.1 g of sodium hydrogencarbonate, 60 ml of water and 60 ml of ethyl acetate. After the mixture had been stirred continuously for 2.5 h, 30 ml of 25% aqueous ammonia solution were added, and the mixture was left to stand for 1 h. The mixture was then adjusted to pH 8 using 10% hydrochloric acid, and the precipitated solid was filtered off and washed with a small amount of ethyl acetate. The organic phase of the combined filtrates was separated off, the aqueous phase was extracted using 2×60 ml of ethyl acetate, and the combined phases were dried over sodium sulfate. Following removal of the solvent under reduced pressure and recrystallization from ethanol, 10.4 g of N-(2-hydroxybenzyl)-N'-(2-hydroxybenzylidene)-N-methyl-1,2-diaminoethane in the form of a yellow, crystalline solid were obtained.

1.84 g of manganese(II) acetate (tetrahydrate) were added in portions to a solution of 2.13 g of this compound in 25 ml of ethanol, and the mixture was refluxed for 2 h. After the reaction solution had cooled, the solvent was removed under reduced pressure and the N-(2-hydroxybenzyl)-N'-(2-hydroxybenzylidene)-N-methyl-1,2-diaminoethane, manganese complex was extracted from the residue using methylene chloride; 3.01 g of black-brown crystals were obtained.

The following metal complexes were prepared in an analogous manner. Where these metal complexes contain cobalt or iron, the compounds were prepared from cobalt(II) acetate (tetrahydrate) or iron(II) acetate.

EXAMPLE 5

N-(2-Hydroxybenzyl)-N'-(3,5-ditert-butyl-2-hydroxybenzylidene)-1,2-diaminoethane, manganese complex

EXAMPLE 6

N-(2-Hydroxybenzyl)-N'-(4-diethylamino-2-hydroxybenzylidene)-1,2-diaminoethane, manganese complex

EXAMPLE 7

N-(2-Hydroxybenzyl)-N'-(2-hydroxy-4-methoxybenzylidene)-1,2-diaminoethane, manganese complex

EXAMPLE 8

N-(2-Hydroxybenzyl)-N'-(2-hydroxy-3-methoxybenzylidene)-1,2-diaminoethane, manganese complex

EXAMPLE 9

N-(2-Hydroxybenzyl)-N'-(2-hydroxy-5-nitrobenzylidene)-1,2-diaminoethane, manganese complex

EXAMPLE 10

N-(2-Hydroxybenzyl)-N'-(3,5-ditert-butyl-2-hydroxybenzylidene)- 1,2-diaminocyclohexane, manganese complex

EXAMPLE 11

N-(2-Hydroxybenzyl)-N'-(3,5-ditert-butyl-2-hydroxybenzylidene)-N-methyl-1,2-diaminoethane, manganese complex

EXAMPLE 12

N-(2-Hydroxybenzyl)-N'-(2-hydroxy-4-methoxybenzylidene)-N-methyl-1,2-diaminoethane, manganese complex

EXAMPLE 13

N-(2-Hydroxybenzyl)-N'-(2-hydroxybenzylidene)-1,2-diamino-ethane, cobalt complex

EXAMPLE 14

N-(2-Hydroxybenzyl)-N'-(3,5-ditert-butyl-2-hydroxybenzylidene)-1,2-diaminoethane, cobalt complex

EXAMPLE 15

N-(2-Hydroxybenzyl)-N'-(2-hydroxy-5-nitrobenzylidene)-1,2-diaminoethane, cobalt complex

EXAMPLE 16

N-(2-Hydroxybenzyl)-N'-(2-hydroxybenzylidene)-1,2-diamino-ethane, iron complex

EXAMPLE 17

N-(2-Hydroxybenzyl)-N'-(3,5-ditert-butyl-2-hydroxybenzylidene)-1,2-diaminoethane, iron complex

EXAMPLE 18

N-(2-Hydroxybenzyl)-N'-(2-hydroxy-5-nitrobenzylidene)-1,2-diaminoethane, iron complex Bleach test A bleach composition was prepared by adding together 200 ml of an aqueous solution of reference laundry detergent WMP (Wäschereiforschungsinstitut Krefeld, [Laundry Research Institute, Krefeld], 5 g/l in water with 15° German water hardness), 150 mg of sodium perborate monohydrate, 50 mg of tetraethylenediamine (TAED) and 2 mg of the corresponding catalyst. Using this composition, swatches with standard soilings (BC-1 tea or IOP paprika on cotton, Laundry Research Institute, Krefeld) were subjected to a treatment at a temperature of 40° C. under isothermal washing conditions in a Linitest apparatus (Heraeus). After a washing time of thirty minutes, the swatches were rinsed with water, dried and ironed; the bleaching action was then quantified by determining the differences $\Delta R_{(CAT-TAED)}$ in reflectances before and after bleaching using an ELREPHO 2000 whiteness measuring device (Datacolor). From these $\Delta R_{(CAT-TAED)}$ values and the $\Delta R_{(TAED)}$ values determined in control experiments without bleach catalyst, the ΔΔ R values listed in Table 1 (standard soiling BC-1 tea) and Table 2 (standard soiling 10P paprika) were calculated, which are a direct measure of the improvement in the bleaching action which has been brought about by the addition of catalyst:

$$\Delta\Delta R = \Delta R_{(Cat-TAED)} - \Delta R_{(TAED)}$$

TABLE 1

| Catalyst from Example No. | 1 | 3 | 4 | 5 | 6 | 7 | 8 | 9 | 10 | 11 | 12 | 13 |
|---|---|---|---|---|---|---|---|---|---|---|---|---|
| ΔΔ R | 2.9 | 3.1 | 2.9 | 2.5 | 5.4 | 3.7 | 3.6 | 3.9 | 3.0 | 3.1 | 3.1 | 2.2 |

TABLE 2

| Catalyst from Example No. | 14 | 15 | 16 | 17 | 18 |
|---|---|---|---|---|---|
| ΔΔ R | 5.3 | 0.1 | 0.4 | 1.0 | 0.1 |

Other advantageous properties of the described complexes are low color damage and low fiber damage.

I claim:

1. A compound of the formula 1

$$[L_n M_m X_p]^z Y_q \quad (1)$$

in which

M is manganese in oxidation stage II, III, IV, V and/or VI or cobalt in oxidation stage II and/or III, or iron in oxidation stage II and/or III, X is a coordination group or bridging group, Y is a counterion in the corresponding stoichiometric amount to balance a charge z present, where z as the metal complex charge can be positive, zero or negative, n and m, independently of one another, are integers from 1 to 4, p is an integer from 0 to 15, q is z/charge of Y L is a ligand of the formula (2)

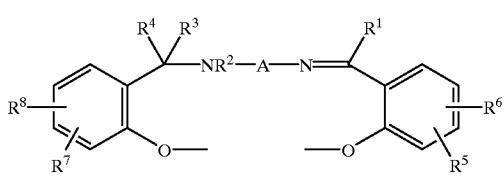

in which $R^1$, $R^2$, $R^3$ and $R^4$ independently of one another are hydrogen, a $C_1$- to $C_{10}$-alkyl, cycloalkyl or aryl radical, $R^5$, $R^6$, $R^7$, $R^8$ independently of one another are hydrogen, $C_1$- to $C_{30}$-alkyl, cycloalkyl or aryl radicals, $C_1$- to $C_4$-alkoxy groups, substituted or unsubstituted amino or ammonium groups, halogen atoms, sulfo groups, carboxyl groups, or groups of the formula —$(CH_2)_r$—COOH, —$(CH_2)_r SO_3 H$, —$(CH_2)_r$—$PO_3 H_2$, —$(CH_2)_r$—OH, in which r and l are integers from 0 to 4, and the specified acid groups may also be in salt form, and A is a $C_2$–$C_4$-alkylene, $C_5$–$C_{10}$-cycloalkylene or arylene group.

2. A compound of the formula 1 as claimed in claim 1, in which X is $F^-$, $Cl^-$, $Br^-$, $SCN^-$, $OH^-$, $O_2^{2-}$, $O^{2-}$, $O_2^-$, $HOO^-$, $R^9OO^-$, $H_2O$, $SH^-$, $CN^-$, $OCN^-$, $S^{2-}$, $N_3^-$, $NH_3$, $NR^9_3$, $NR^9_2$, $R^9O^-$, $R^9COO^-$, $R^9SO_3^-$ and $R^9SO_4^-$, in which $R^9$ is in each case hydrogen, $C_1$- to $C_8$-alkyl, cycloalkyl or $C_6$- to $C_{18}$-aryl.

3. A compound of the formula 1 as claimed in claim 1 in which the counterion Y is $F^-$, $Cl^-$, $Br^-$, $NO_{3-}$, $ClO_4^-$, $SCN^-$, $PF_6^-$, $R^9SO_4^-$, $R^9COO^-$, $R^9SO_3^-$, $BF_4^-$, $BPh_4^-$, $SO_4^{2-}$ and $SO_4^{2-}$; $Li^+$, $Na^+$, $K^+$, $Mg^{2+}$, $Ca^{2+}$, $Al^{3+}$, $NH_4^+$, $R^9NH_3^+$, $R^9_2NH_2^+$, $R^9_3NH^+$ and $R^9_4N^+$, and $R^9$ is as defined in claim 2.

4. A compound of the formula 1 as claimed in claim 1, in which A is an ethylene group or cyclohexylene group.

5. A compound of the formula 1 as claimed in claims 1 to 3, in which $R^1$, $R^2$, $R^3$, $R^4$, $R^6$, $R^7$ and $R^8$ are hydrogen, and $R^5$ is a $C_1$–$C_4$-alkyl, $C_1$–$C_4$-alkoxy or a substituted or unsubstituted amino or ammonium group.

6. A compound of the formula 1 as claimed in claim 1, in which $R^1$, $R^2$, $R^3$, $R^4$, $R^6$, $R^7$ and $R^8$ are hydrogen, and $R^5$ is a di-$C_1$–$C_4$-alkylamino group.

7. A compound of the formula 1 as claimed in claim 1, in which M is manganese in oxidation stage II, III, IV, V or VI, m and n are each 1 and p is an integer from 0 to 3.

8. A compound of the formula 1 as claimed in claim 1, in which M is manganese in oxidation stage II or III, m and n are each 1 and p is an integer from 0 to 3.

9. A compound of the formula 1 as claimed in claim 1, in which M is manganese in oxidation stage II, III, IV, V and/or VI, m is 2, n is 1 or 2 and p is an integer from 0 to 5.

10. A compound of the formula 1 as claimed in claim 1, in which M is manganese in oxidation stage II and/or III, m is 2, n is 1 or 2 and p is an integer from 0 to 5.

11. A compound of the formula 1 as claimed in claim 1, in which M is cobalt in oxidation stage II or III, m and n are each 1 and p is an integer from 0 to 3.

12. A compound of the formula 1 as claimed in claim 1, in which M is cobalt in oxidation stage II or III, m and n are each 1 and p is zero.

13. A process for using the compounds of the formula 1 as claimed in claim 1 as bleach catalysts and oxidation catalysts with a peroxy compound in a pulverulent or liquid bleach comprising contacting a substrate with said compound and said peroxy compound.

14. A process for bleaching a soiled substrate comprising contacting the soiled substrate with a detergent comprising a bleaching peroxide and the compound of the formula 1 as claimed in claim 1.

15. A process for cleaning a surface comprising applying the compound of the formula 1 as claimed in claim 1 in a detergent formulation to said surface.

16. A process for bleaching textile or paper comprising applying to said textile or paper a peroxy bleach compound in an aqueous bleaching liquor with the compound of the formula 1 as claimed in claim 1.

* * * * *